United States Patent [19]

Baker

[11] Patent Number: 6,036,950

[45] Date of Patent: *Mar. 14, 2000

[54] METHOD FOR IMPROVING UTILISATION OF NUTRIENTS BY RUMINANT OR RUMINANT-LIKE ANIMALS

[75] Inventor: Suzanne Kay Baker, West Perth, Australia

[73] Assignee: Commonwealth Scientific and Industrial Research Organisation, Parkville, Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/633,776

[22] PCT Filed: Oct. 19, 1994

[86] PCT No.: PCT/AU94/00633

§ 371 Date: Apr. 19, 1996

§ 102(e) Date: Apr. 19, 1996

[87] PCT Pub. No.: WO95/11041

PCT Pub. Date: Apr. 27, 1995

[30] Foreign Application Priority Data

Oct. 19, 1993 [AU] Australia ................................. PM1901

[51] Int. Cl.[7] .......................... A61K 39/00; A61K 39/02; A01N 63/00; A01N 37/18

[52] U.S. Cl. .................. 424/93.1; 424/184.1; 424/234.1; 514/2

[58] Field of Search .............................. 424/130.1, 184.1, 424/234.1, 93.1; 514/2

[56] References Cited

U.S. PATENT DOCUMENTS 5,091,364 2/1992 Baumgarten et al. ....................... 514/8
5,648,258 7/1997 Odom ................................... 435/252.1

FOREIGN PATENT DOCUMENTS 602348 3/1988 Australia .
0206942 12/1986 European Pat. Off. .

OTHER PUBLICATIONS

Burgess et al (J Cell Bio, 111: 2129–2138), 1990.
Lazar et al (Mol & Cell Bio, 8: 1247–1252, 1988.
Tao et al (J. Immunol 143:2595–2601, 1989.
Harlow & Lane (Antibodies, A Lab. Manual, Cold Spring Harbor Lab, NY, pp. 96 & 97, 1988.

*Primary Examiner*—Paula K. Hutzell
*Assistant Examiner*—Susan Ungar
*Attorney, Agent, or Firm*—Jacobson, Price, Holman & Stern, PLLC

[57] ABSTRACT

A method for improving the nutrient uptake of a ruminant or ruminant-like animal comprising inoculating the animal with an immunogenic preparation effective in inhibiting the activity in the gastrointestinal tract of at least one species or strain of Archae. The immunogenic preparation comprises an antigen component prepared from methanogenic bacteria.

18 Claims, 3 Drawing Sheets

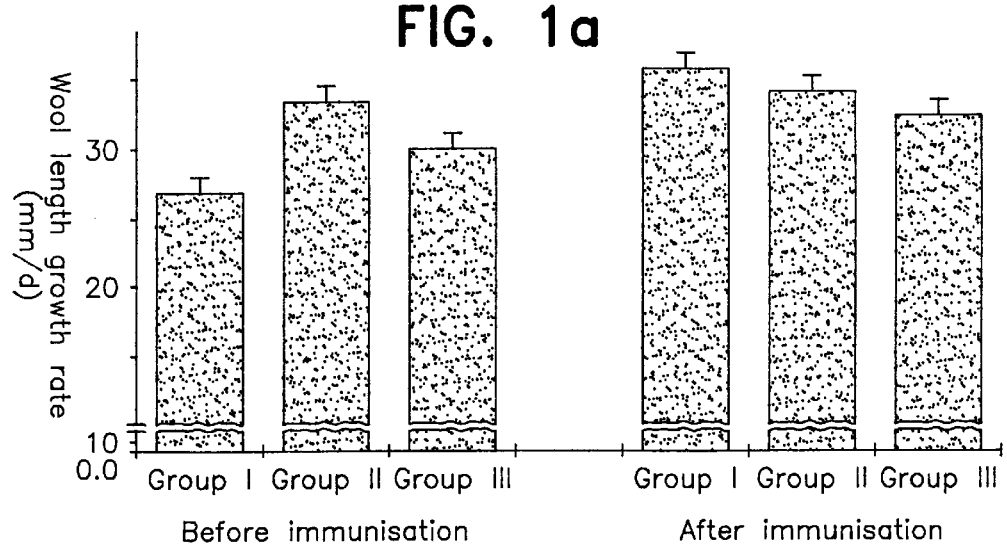
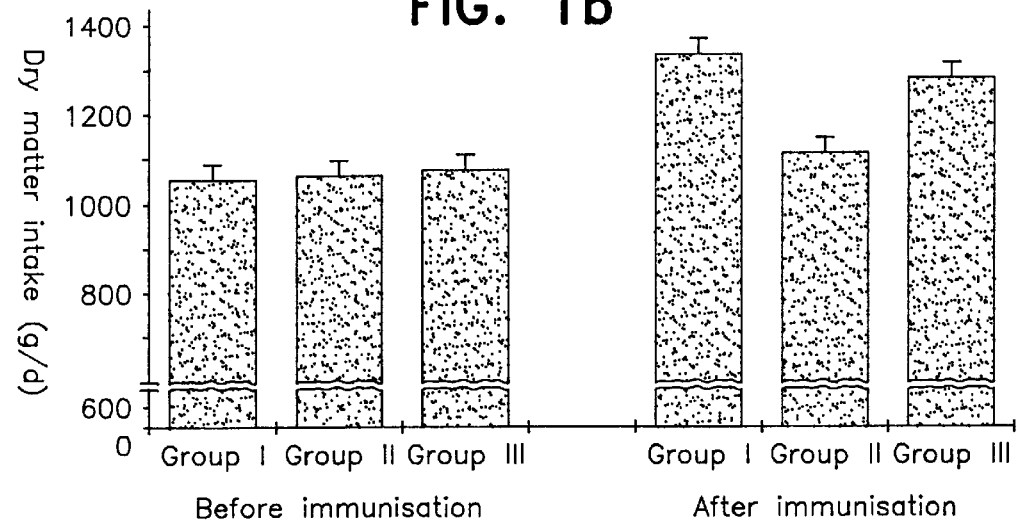
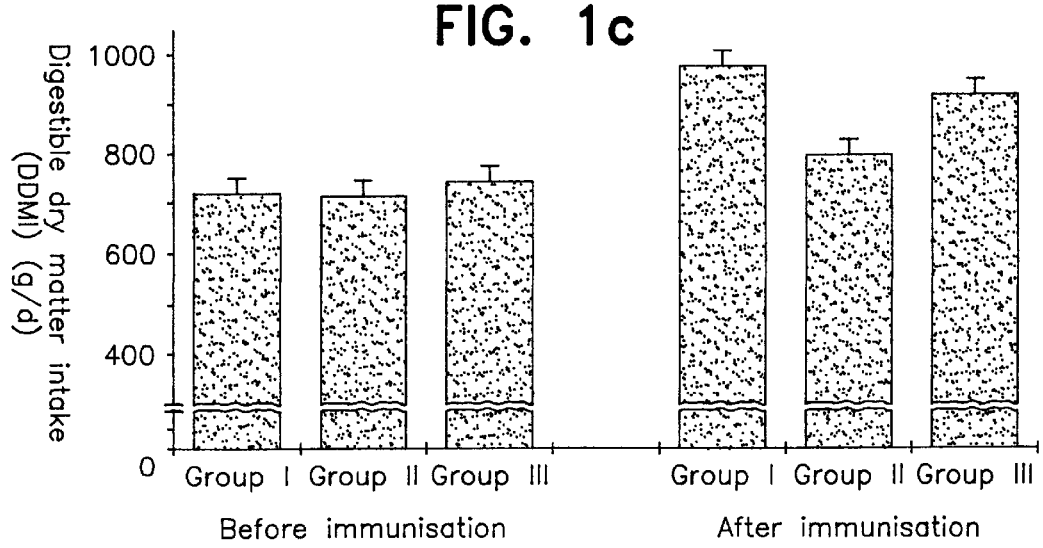

METHOD FOR IMPROVING UTILISATION OF NUTRIENTS BY RUMINANT OR RUMINANT-LIKE ANIMALS

FIELD OF THE INVENTION

This invention relates to methods for improving the utilisation of nutrients by ruminant and ruminant-like animals.

BACKGROUND OF THE INVENTION

The rumen or forestomach is an organ found in the digestive tract of certain herbivorous mammals prior to the gastric stomach and within which the digestion and fermentation of plant material occurs through the activity of special microbial populations. A group of which some are found amongst such microbial populations are the Archae.

The Archae are a diverse group with regard to their physiology and include the methanogens, halophiles and thermacidophiles. They are related through ribosomal RNA sequences that differ drastically from those of other procaryotes. Because of the anaerobic conditions in the rumen only those Archae that are obligate anaerobes are found therein. One member of the Archae found in the rumen, the methanogens are able to produce methane in symbiosis with other rumen microorganisms. For example, $H_2$ and $CO_2$ are common end products and these may subsequently be used by the methanogens in the production of methane.

It has been recognised for some time, see e.g. Baxter, K. L. (1962) 'The Energy Metabolism of ruminants' (Hutchinson, London), that rumen methanogenesis can result in a loss of energy available to an animal, a loss equivalent to possibly 10% of an animal's gross energy intake. To reduce this loss several procedures for the inhibition of methanogenesis in the rumen have been investigated over the years. These procedures include the use of feed additives such as long-chain unsaturated fatty acids and the administration of ionophoric drugs to inhibit the production of $H_2$. Varying degrees of inhibition of methanogenesis have been demonstrated although in no case has it been clearly established that the overall result was economically favourable. Furthermore, irrespective of any technical inadequacies, the concept of constant administration of feed additives and drugs to meat-producing animals is increasingly regarded with disfavour by meat consumers.

SUMMARY OF THE INVENTION

In accordance with a first aspect of the present invention there is provided a method for improving the nutrient uptake of a ruminant or ruminant-like animal comprising inoculating the animal with an immunogenic preparation effective in inhibiting the activity in the gastro-intestinal tract of at least one species or strain of Archae.

The ruminant animal may be a bovine, ovine, caprine, or cervine, while the ruminant-like animal may be a macropod, llama or alpaca.

The immunogenic preparation may comprise a whole cell preparation or a whole cell extract of one or more purified species or strains of Archae. Additionally, or alternatively, the preparation may comprise an immunogenic fraction(s), polypeptide(s)/peptide(s) polysaccharide(s) or lipopolysaccharide(s) derived from one or more species or strains of Archae. Preferably the immunogenic preparation is effective in inhibiting the activity in the gastrointestinal tract of many species and strains of Archae, including the methanogenic bacteria.

The immunogenic preparation may further comprise one or more adjuvants of the type commonly used in the art, and may be provided as a veterinary preparation comprising an antigen component derived from one or more species or strains of Archae.

The immunogenic preparation or vaccine may be administered to the ruminant or ruminant-like animal via the intraperitoneal, intravenous or sub-cutaneous routes.

With regard to the method of the invention, the anaerobic fermentation of carbohydrates in the rumen results in the formation of volatile fatty acids, carbon dioxide and methane. In this respect, it has been demonstrated that there is an inverse relationship between the production of methane and the production of propionate by rumen microorganisms. Indeed, wool production responds more to the supply of protein (which is spared by propionate) to the abomasum than to the supply of energy and, accordingly, the present invention may be expected to enhance wool growth in sheep.

Additionally, through a reduction in methane production the present invention may also provide benefits due to the belief that methane is a significant contributor to the "greenhouse" effect.

In particular, the method of the present invention makes it possible for animals to have an improved productivity and nutrient uptake. In this respect, and as will be illustrated by the example below, animals to which the method is applied show improved characteristics, such as improved wool length growth (for sheep) and show an increased voluntary intake of dry matter and digestible dry matter, thereby increasing nutrient uptake. These aspects of improved productivity and nutrient uptake are improvements over the normal characteristics of those same animals when not subjected to the method of the invention.

However, and with this in mind, because the Archae, including the methanogens, are naturally present in the rumen or forestomach of the vast majority of ruminant and ruminant-like animals it will be appreciated that animals exposed to the present invention are thus considered healthy animals and actually signify the normal population of any given animal species.

BRIEF DESCRIPTION OF THE DRAWINGS

FIG. 1a is a graph showing the wool length growth rate (mm/day) in different groups of sheep, before and after inoculation with, Group I, the vaccine and Groups II and III, PBS alone.

FIG. 1b is a graph showing the dry matter intake (g/day) in different groups of sheep, before and after inoculation with, Group I, the vaccine and Groups II and III, PBS alone.

FIG. 1c is a graph showing the digestible dry matter intake (g/day) in different groups of sheep, before and after inoculation with, Group I, the vaccine and Groups II and III, PBS alone.

DESCRIPTION OF PREFERRED EMBODIMENTS

Figure 1D:
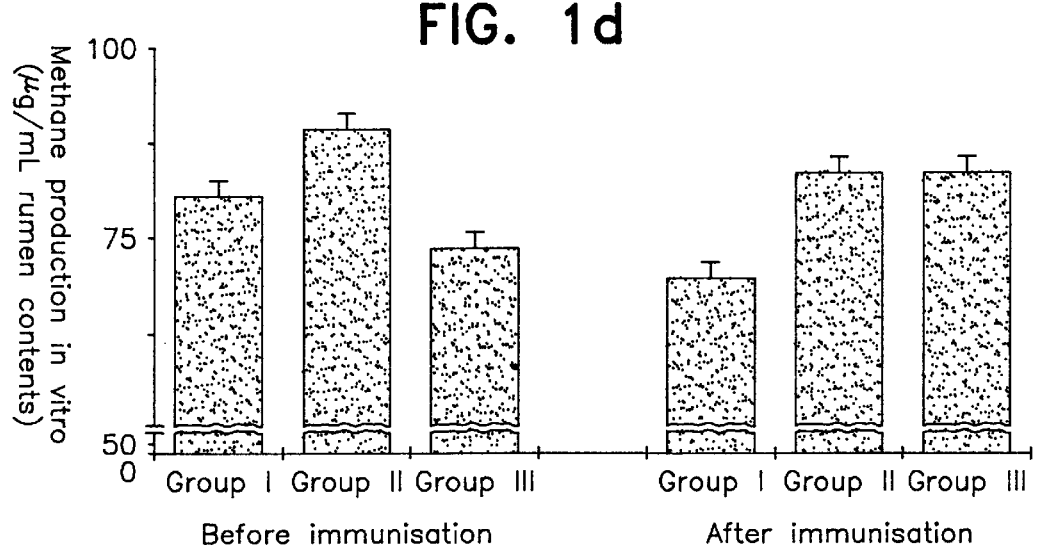
FIG. 1d is a graph showing methane productions in vitro (ug/ml rumen contents) in different groups of sheep, before and after inoculation with, Group I, the vaccine and Groups II and III, PBS alone.

The present invention will now be described, by way of example only, in relation to two examples. The examples illustrate various aspects of the present invention, but are in no way intended to limit the scope thereof.

EXAMPLE 1

Response of Sheep to the Intraperitoneal Administration of Antigen and Adjuvant

An experiment was conducted using three test groups of ten (10) weaner wethers. The test groups are defined as follows:

Group I vaccine (antigen and adjuvant) administered intraperitoneally

Group II adjuvant plus phosphate-buffered saline (PBS) administered intraperitoneally (control)

Group III phosphate buffered saline (PBS) administered intraperitoneally (control)

The vaccine was prepared from formaldehyde-killed cells of the following Archae:

*Methanobacter formicium* (strain MF);

*Methanobrevibacter arboriphilus* (strains AZ, DH1 and DC);

*Methanobrevibacter ruminantium* (strains M1 and Z6);

*Methanobrevibacter smithii* (strains AL1-A, B181 and PS); and

*Methanosarcina barkeri* (strain MS).

Approximately $2 \times 10^9$ cells of each strain were combined, washed and resuspended in 20 ml sterile phosphate-buffered saline (PBS) (pH7.2). Finally, an emulsion of 10 ml of this preparation (the antigen) and 10 ml Freund's complete adjuvant (FCA) was made, forming the vaccine used. The vaccine was administered (1.5 ml per animal) as a primary inoculation intraperitoneally at the sub-lumbar fossa on the right mid-flank. The booster inoculation (1.5 ml per animal) was given subcutaneously twenty eight (28) days later, using the antigen preparation described above without added adjuvant (FCA).

The two control test groups were administered:

i) Freund's's complete adjuvant (FCA) emulsified in an equal volume of PBS (1.5 ml per animal)—Group II; and ii) sterile PBS alone (1.5 ml per animal)—Group III.

Each of i) and ii) were administered by the same route as the vaccine of Group I. The booster inoculation in each of test Groups II and III was sterile PBS alone (1.5 ml per animal) administered subcutaneously twenty eight (28) days after the primary inoculation.

The sheep were offered an ad libitum diet comprised of 80% oaten hay, 10% oat grain, 7% lupin grain, 1% urea and 2% mineral mix (sold under the brand name "Siromin"). Voluntary intake of dry matter was measured daily.

Live weight was measured every two weeks and the length growth rate of t he wool was determined using dyebands applied at approximately four-week intervals. As noted above, the primary inoculation was followed by the second or booster inoculation 28 days later. The digestibility of the diet was measured before and after the treatments were administered (ie. before and after the sheep were inoculated).

The methane production of the microbial population from the rumen of each sheep was determined in vitro before and after each sheep was inoculated. An aliquot of rumen contents, obtained using a stomach tube, was incubated for 24 hours at 37° C. in a culture broth of sterilised rumen liquor under an atmosphere of nitrogen and carbon dioxide. The methane content of the gases evolved during incubation was determined by gas chromatography.

The measurements made during the period prior to inoculation of the sheep were used as covariates in the statistical analysis of the measurements made after the sheep were inoculated.

FIG. 1a illustrates the differences in the wool length growth rate (mm/day), between sheep in the above groups before and after inoculation. The wool length growth rate was greater in sheep given the vaccine (Group I) than in the control groups, for example the sheep given PBS alone ($p<0.02$).

FIG. 1b illustrates the differences in the dry matter intake (g/day), between sheep in the above groups before and after inoculation. Sheep inoculated with the vaccine (Group I) showed a significant increase in dry matter intake compared to those administered the adjuvant and PBS (Group II) ($p<0.009$).

FIG. 1c illustrates the differences in the digestible dry matter intake (g/day), between sheep in the above groups before and after inoculation. Inoculated sheep (Group 1) showed a significant increase in digestible dry matter intake ($p<0.002$) compared to those administered the adjuvant and PBS (Group II).

FIG. 1d illustrates the differences in methane production in vitro (ug/ml inoculum of rumen contents), between sheep in the above groups before and after inoculation. A significant ($p<0.018$) reduction in methane production is evident in samples taken from sheep given the vaccine (Group I) compared with those samples taken prior to inoculation with the vaccine. In addition, there is a significantly lower production of methane in samples taken from sheep administered vaccine (Group I) compared with those samples taken from sheep in Group II or in Group III ($P<0.018$).

Figure 1E:
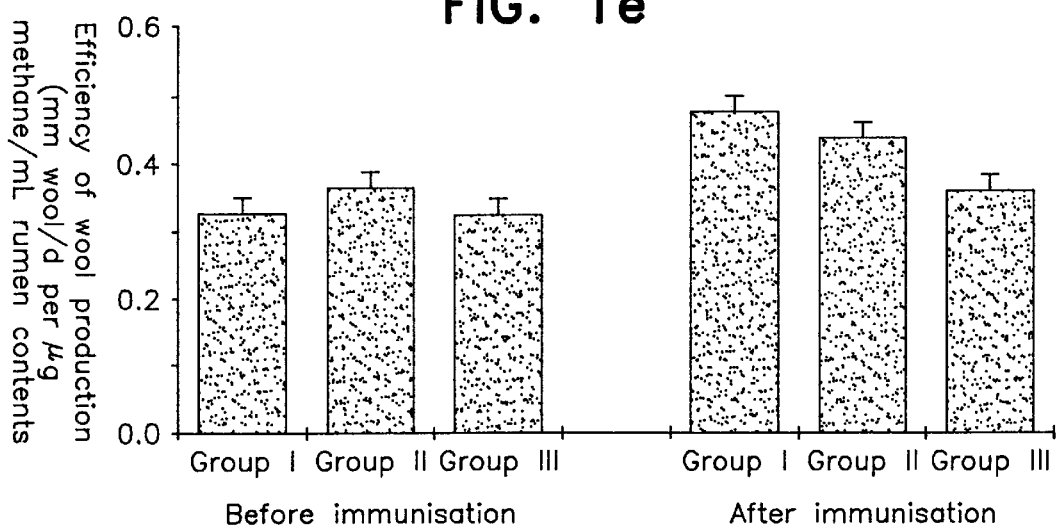
FIG. 1e is a graph showing efficiency of wool production expressed in wool length growth rate (mm/day) in different groups of sheep, before and after inoculation with, Group I, the vaccine and Groups II and III, PBS alone.

FIG. 1e illustrates the differences in efficiency of wool production, expressed as length growth rate of wool (mm/d) relative to methane produced in vitro ($\mu g$/ml of rumen contents) in the above groups before and after inoculation. A significant ($p=0.09$) increase in efficiency of wool production is evident in sheep given the vaccine (Group 1) compared with those administered PBS alone (Group III).

Figure 1F:
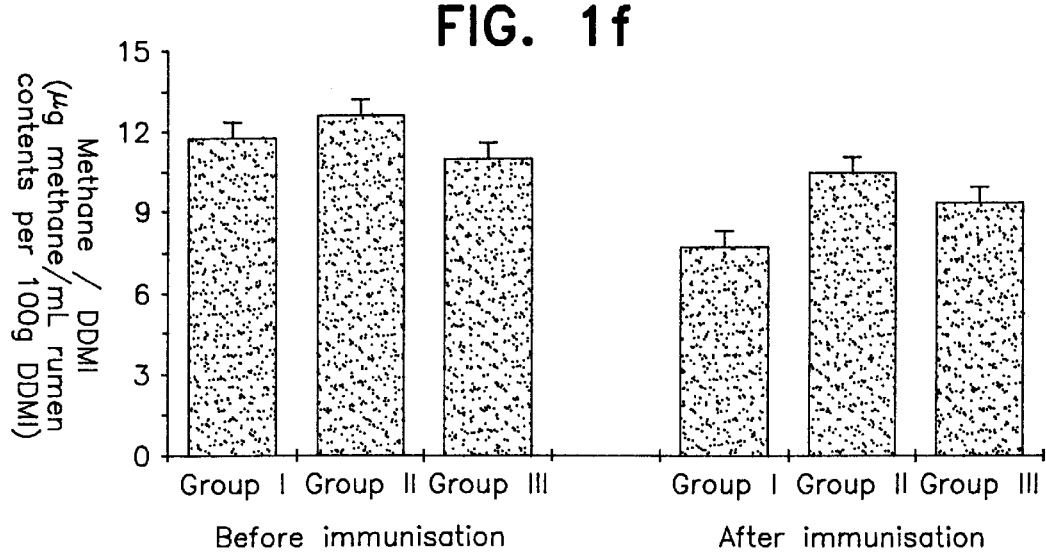
FIG. 1f is a graph showing methane production in vitro (ug/ml of rumen contents) relative to digestible dry matter intake in different groups of sheep, before and after inoculation with, Group I, the vaccine and Groups II and III, PBS alone.

FIG. 1f illustrates the differences in methane production in vitro ($\mu g$/ml) rumen contents) relative to digestible dry matter intake in the above groups before and after inoculation. A significant reduction ($p<0.06$) in methane produced per 100 g digestible dry matter intake (DDMI) is evident in sheep given the vaccine (Group I) compared with those administered the adjuvant and PBS (Group II).

EXAMPLE 2

Immunoglobulin Levels in Sheep after the Intraperitoneal Administration of an Antigen/Adjuvant Vaccine.

An experiment was conducted using three test groups of eight (8) weaner wethers. Three vaccines were prepared, each using an antigen prepared from a washed preparation of mixed rumen protozoa and administered to a separate test group. Frozen whole cells were thawed and 20 ml fractions ($10^6$ cells/ml) were incorporated into three vaccines as follows:

i) Freund's vaccine comprising 20 ml of the antigen preparation emulsified with 20 ml of Freund's Complete Adjuvant (FCA). The dose administered was 3 ml per animal;

ii) Alum vaccine comprising 20 ml of the antigen preparation incorporated with "Alhydrogel" (Superfos, Denmark) according to the manufacturer's directions. The dose administered was 2.5 ml per animal; and iii) DEAE-dextran sulphate vaccine comprising 20 ml of the antigen preparation, 20 ml of 20% (w/v) diethlaminoethyl (DEAE)-dextran sulphate, 1 ml of 30% (v/v) glycerol, 1 ml of 1% (v/v) Tween 80 and 35 ml squalene mixed together. The mix formed an emulsion containing oil droplets no larger than 40 um in diameter. The dose administered was 5 ml per animal.

Each vaccine i), ii) and iii) was administered intraperitoneally at the sub-lumbar fossa on the right mid-flank of the animal for the primary inoculation. The booster inoculation in each case comprised a volume of the antigen preparation plus an equal volume of sterile PBS, being 1.5 ml administered subcutaneously 80 days after the primary inoculation.

A titre of antibody (IgG) was measured in both serum and saliva obtained from each animal on days 10, 21 and 113 after primary inoculation.

Figure 2A:
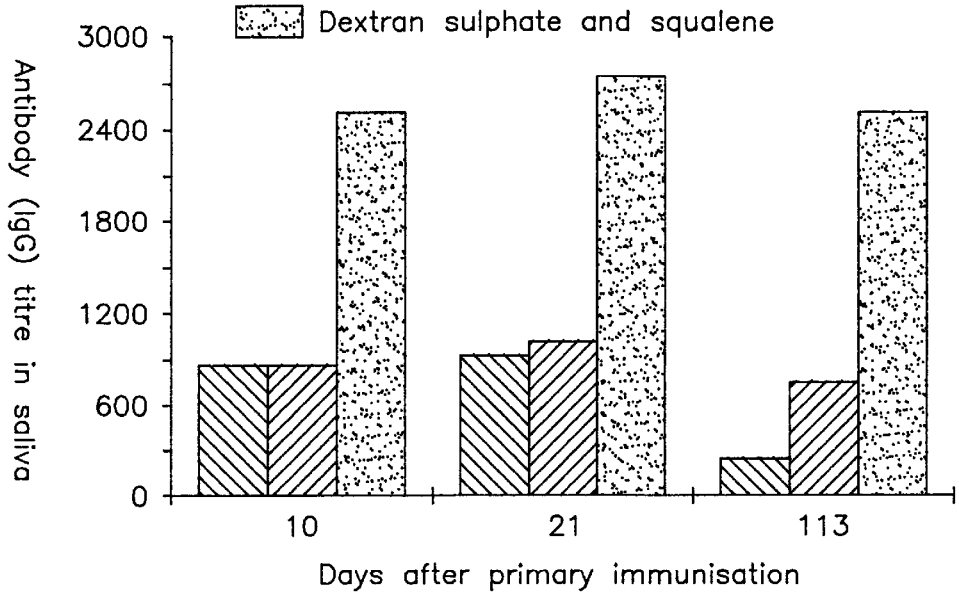
FIG. 2a is a graph showing the IgG levels (titre) present in saliva obtained from animals administered with i) DEAE-dextran sulphate vaccine compared to ii) vaccine of Freund's complete adjuvant and iii) vaccine of Alum, taken at 10, 21 and 113 days after primary immunization.

FIG. 2a illustrates the significantly potentiated and sustained IgG levels (titre) in saliva obtained from animals administered the DEAE-dextran sulphate vaccine at each of the 10, 21 and 113 day samples compared with those of animals administered either vaccines i) or ii).

Figure 2B:
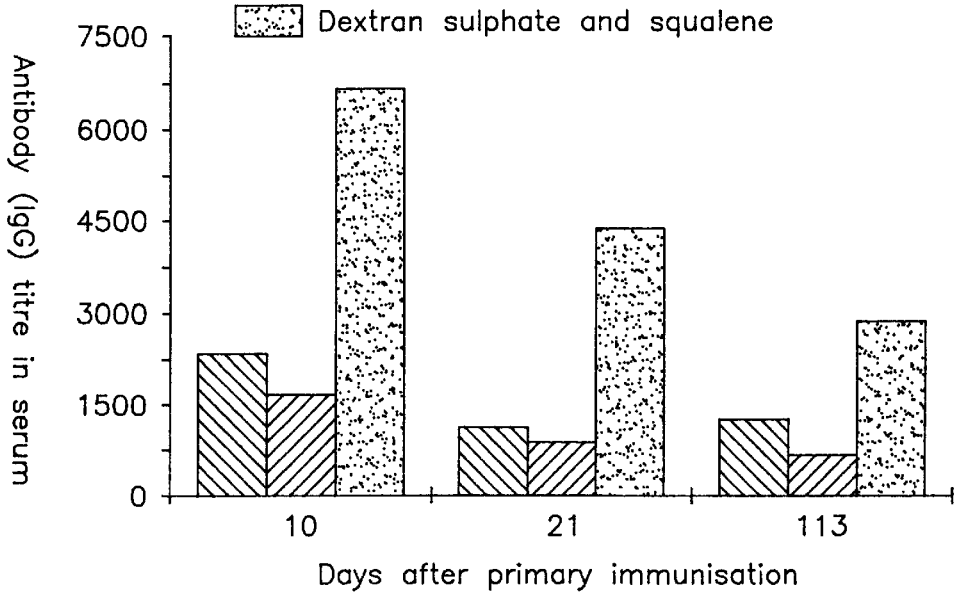
FIG. 2b is a graph showing the IgG levels (titre) present in serum obtained from animals administered with i) DEAE-dextran sulphate vaccine, before and after inoculation with, Group I, the vaccine and Groups II and III, PBS alone.

FIG. 2b illustrates the significantly potentiated IgG levels (titre) in serum obtained from animals administered with the DEAE-dextran sulphate vaccine at each of the 10, 21 and 113 day samples compared with those of animals administered either vaccines i) or ii).

It is evident from the above example that a DEAE-dextran and mineral oil, squalene or squalane emulsion when used as an immunoadjuvant together with an antigen prepared from washed rumen protozoa is capable of eliciting antibody titres approximately three (3) times greater than those obtained when FCA is used as the adjuvant in a vaccine administered to sheep (this represents a special or particular variation of the disclosure of International Application No. PCT/AU87/00250 (WO 88/01177)). It is envisaged that similar results will be obtained if Archae, for example methanogens, are used as the antigen, or are used to produce the antigen. Such results are considered significant because whilst FCA is considered one of the most powerful immunoadjuvants presently available, it has not found wide application outside the laboratory because of the adverse tissue reaction it provokes in recipient animals, including the production of granulomateous lesions at the site of inoculation.

Accordingly, it is expected that the immunogenic activity of a vaccine produced from Archae and a combination of DEAE-dextran and an immunoadjuvant oil such as a mineral oil, squalane or squalene will be similarly effective in generating antibody titres that compare with those elicited when Archae and FCA are used as the antigen/adjuvant combination in the preparation of a vaccine. As such, it is envisaged that given such a immunogenic activity in such a vaccine there will be a significant inhibition of activity in the gastro-intestinal tract of one or more species or strains of Archae, dependent upon which species or strains were used to prepare the antigen employed in the vaccine, and which does not have the adverse reactions seen when FCA is used.

It is further envisaged that similarly significant levels of the growth rate of wool, dry matter intake and digestible dry matter intake may be achieved when compared with the levels demonstrated using a FCA vaccine in Example 1.

It is still further envisaged that the present invention, through the inhibition of methane production, provides the opportunity to (i) manipulate body composition of ruminants by improving the balance of protein and energy supplied to an animal; and (ii) provide leaner carcasses in lot-fed animals.

Modifications and variations such as would be apparent to the skilled addressee upon a reading of this specification are considered to fall within the scope of the present invention.

We claim:

1. A method for increasing the nutrient uptake of a ruminant or ruminant-like animal selected from the group consisting of macropod, llama and alpaca comprising administering to the animal an immunogenic preparation containing a whole cell preparation or whole cell extract of at least one species of methanogenic Archae.

2. The method according to claim 1, wherein the at least one methanogenic Archae is a member of a genus selected from the group consisting of Methanobacter, Methanobrevibacter and Methanosarcina.

3. The method according to claim 1, wherein the at least one methanogenic Archae is selected from the group consisting of *Methanobacter formicium, Methanobrevibacter arboriphilus, Methanobrevibacter ruminantium, Methanobrevibacter smithii* and *Methanosarcina barkeri*.

4. A method according to claim 1, wherein the methanogenic Archae is *Methanobacter formicium*.

5. The method according to claim 1, wherein the whole cell preparation or whole cell extract is from a killed cell preparation.

6. The method according to claim 5, wherein the killed cell preparation comprises a formaldehyde killed cell preparation.

7. The method according to claim 1 wherein the immunogenic preparation contains whole cell preparation or whole cell extract from a plurality of species of methanogenic Archae.

8. The method according to claim 1 wherein the immunogenic preparation further comprises a suitable adjuvant.

9. The method according to claim 8, wherein the adjuvant contains DEAE-dextran.

10. The method according to claim 9, wherein the adjuvant further contains an immunoadjuvant oil.

11. The method according to claim 10, wherein the immunoadjuvant oil is one or more of a mineral oil, squalene and squalane.

12. The method according to claim 1, wherein the immunogenic preparation is administered intraperitoneally.

13. The method according to claim 1, wherein the administration of the immunogenic preparation to the animal comprises a primary inoculation with the immunogenic preparation and an adjuvant administered via the intraperitoneal route and a secondary or booster inoculation with immunogenic preparation alone.

14. The method according to claim 1, wherein the administration with the immunogenic preparation provides an increase in the efficiency of utilization of nutrients upon an inhibition of methane production.

15. The method according to claim 14, wherein the increased efficiency includes a statically significant increase in the length growth rate of wool relative to methane production.

16. The method according to claim 14, wherein the increased efficiency includes a statically significant decrease in methane production relative to digestible dry matter intake.

17. The method according to claim 1, wherein the methanogenic Archae is *Methanobacter formicium, Methanobrevibacter ruminantium* and *Methanosarcinia barkeri.*

18. A method for inhibiting methane production in a ruminant or ruminant-like animal selected from the group consisting of macropod, llama and alpaca comprising administering to the animal an immunogenic preparation containing a whole cell preparation or whole cell extract of at least one species of methanogenic Archae.

* * * * *